(12) United States Patent
Ofer

(10) Patent No.: US 12,167,198 B2
(45) Date of Patent: *Dec. 10, 2024

(54) METHODS AND SYSTEMS FOR AUDITORY NERVE SIGNAL CONVERSION

(71) Applicant: Moshe Ofer, Ramat Hasharon (IL)

(72) Inventor: Moshe Ofer, Ramat Hasharon (IL)

(*) Notice: Subject to any disclaimer, the term of this patent is extended or adjusted under 35 U.S.C. 154(b) by 0 days.

This patent is subject to a terminal disclaimer.

(21) Appl. No.: 18/118,233

(22) Filed: Mar. 7, 2023

(65) Prior Publication Data

US 2023/0209279 A1 Jun. 29, 2023

Related U.S. Application Data

(63) Continuation of application No. 17/728,013, filed on Apr. 25, 2022, now Pat. No. 11,641,555.

(60) Provisional application No. 63/215,569, filed on Jun. 28, 2021.

(51) Int. Cl.
*H04R 25/00* (2006.01)

(52) U.S. Cl.
CPC ......... *H04R 25/35* (2013.01); *H04R 2225/67* (2013.01)

(58) Field of Classification Search
CPC ............... A61N 1/0529; A61N 1/0541; A61N 1/36038; H04R 2460/01; A61B 5/125
See application file for complete search history.

(56) References Cited

U.S. PATENT DOCUMENTS

| | | | |
|---|---|---|---|
| 5,178,161 A | 1/1993 | Kovacs | |
| 6,175,767 B1 | 1/2001 | Doyle, Sr. | |
| 6,728,578 B1 * | 4/2004 | Voelkel | A61N 1/36038 607/55 |
| 7,991,475 B1 | 8/2011 | Tang et al. | |
| 8,369,958 B2 * | 2/2013 | Kwon | A61N 1/36038 607/57 |
| 9,327,120 B2 * | 5/2016 | Richter | A61N 1/37217 |
| 9,451,883 B2 * | 9/2016 | Gallant | A61B 5/0075 |
| 9,480,582 B2 | 11/2016 | Lundborg | |

(Continued)

FOREIGN PATENT DOCUMENTS

| | | |
|---|---|---|
| CN | 103705229 A | 4/2014 |
| CN | 204520668 U | 8/2015 |
| WO | 2020242888 A1 | 12/2020 |

OTHER PUBLICATIONS

Robert Sanders, "Editing brain activity with holography," Apr. 30, 2018, Berkeley News (Year: 2018).

*Primary Examiner* — Ryan Robinson
(74) *Attorney, Agent, or Firm* — Rivka Friedman

(57) ABSTRACT

A processing device is interfaced with an auditory region of the brain of a subject that is responsible for auditory perception. The processing device receives signals associated with nerve impulses that are transmitted to the auditory region of the brain of the subject in response to sound collected by an ear of the subject. The processing device processes the received signals and generates at least one audio signal that is representative of the auditory perception, by the subject, of the sound collected by the ear. In certain embodiments, the processing device processes at least one audio signal that is representative of at least one sound to convert the at least one audio signal to a sequence of nerve impulses, and selectively provides the sequence of nerve impulses to the auditory region of the brain of the subject such that the subject audially perceives the at least one sound.

20 Claims, 4 Drawing Sheets

(56) References Cited

U.S. PATENT DOCUMENTS

| | | |
|---|---|---|
| 10,123,133 B2 | 11/2018 | Pontoppidan et al. |
| 10,264,990 B2 * | 4/2019 | Pasley .................. A61B 5/6814 |
| 10,441,172 B2 | 10/2019 | Tanaka |
| 10,925,509 B2 | 2/2021 | Nestor |
| 11,071,465 B2 | 7/2021 | Angle et al. |
| 11,373,672 B2 * | 6/2022 | Mesgarani ........... H04R 25/507 |
| 11,395,620 B1 | 7/2022 | Moshe |
| 11,467,665 B2 | 10/2022 | Gribetz |
| 2004/0155112 A1 * | 8/2004 | Matsuda .......... H04N 21/41407 |
| | | 235/472.02 |
| 2004/0172098 A1 | 9/2004 | Greenberg |
| 2005/0283202 A1 | 12/2005 | Gellman |
| 2008/0161915 A1 | 7/2008 | Ren |
| 2008/0242950 A1 | 10/2008 | Jung |
| 2008/0319276 A1 | 12/2008 | Jung |
| 2009/0216091 A1 | 8/2009 | Arndt |
| 2010/0026798 A1 | 2/2010 | Schmid |
| 2011/0144471 A1 | 6/2011 | Hsu |
| 2011/0227586 A1 | 9/2011 | Lovetri |
| 2013/0131537 A1 * | 5/2013 | Tam ....................... A61B 5/377 |
| | | 600/544 |
| 2013/0184558 A1 | 7/2013 | Gallant |
| 2014/0214120 A1 | 7/2014 | Simon |
| 2014/0267401 A1 | 9/2014 | Urbach |
| 2015/0119689 A1 | 4/2015 | Pascual-Leone |
| 2015/0142082 A1 | 5/2015 | Simon |
| 2015/0248470 A1 | 9/2015 | Coleman |
| 2016/0073887 A1 | 3/2016 | Lee |
| 2016/0109851 A1 | 4/2016 | Tsang |
| 2017/0087367 A1 | 3/2017 | Weisend |
| 2018/0021579 A1 | 1/2018 | Kahana |
| 2018/0200389 A1 | 7/2018 | Wong |
| 2018/0245097 A1 | 8/2018 | Vogel |
| 2018/0304095 A1 | 10/2018 | Register |
| 2019/0082990 A1 | 3/2019 | Poltorak |
| 2019/0227490 A1 | 7/2019 | Waller |
| 2019/0336060 A1 | 11/2019 | Shen |
| 2019/0357797 A1 | 11/2019 | Nestor |
| 2020/0187841 A1 * | 6/2020 | Ayyad .................... A61B 5/377 |
| 2020/0196932 A1 | 6/2020 | Johnson |
| 2021/0293714 A1 | 9/2021 | Matoba |
| 2022/0248148 A1 * | 8/2022 | Verhulst ............... H04R 25/507 |
| 2022/0417678 A1 | 12/2022 | Moshe |

\* cited by examiner

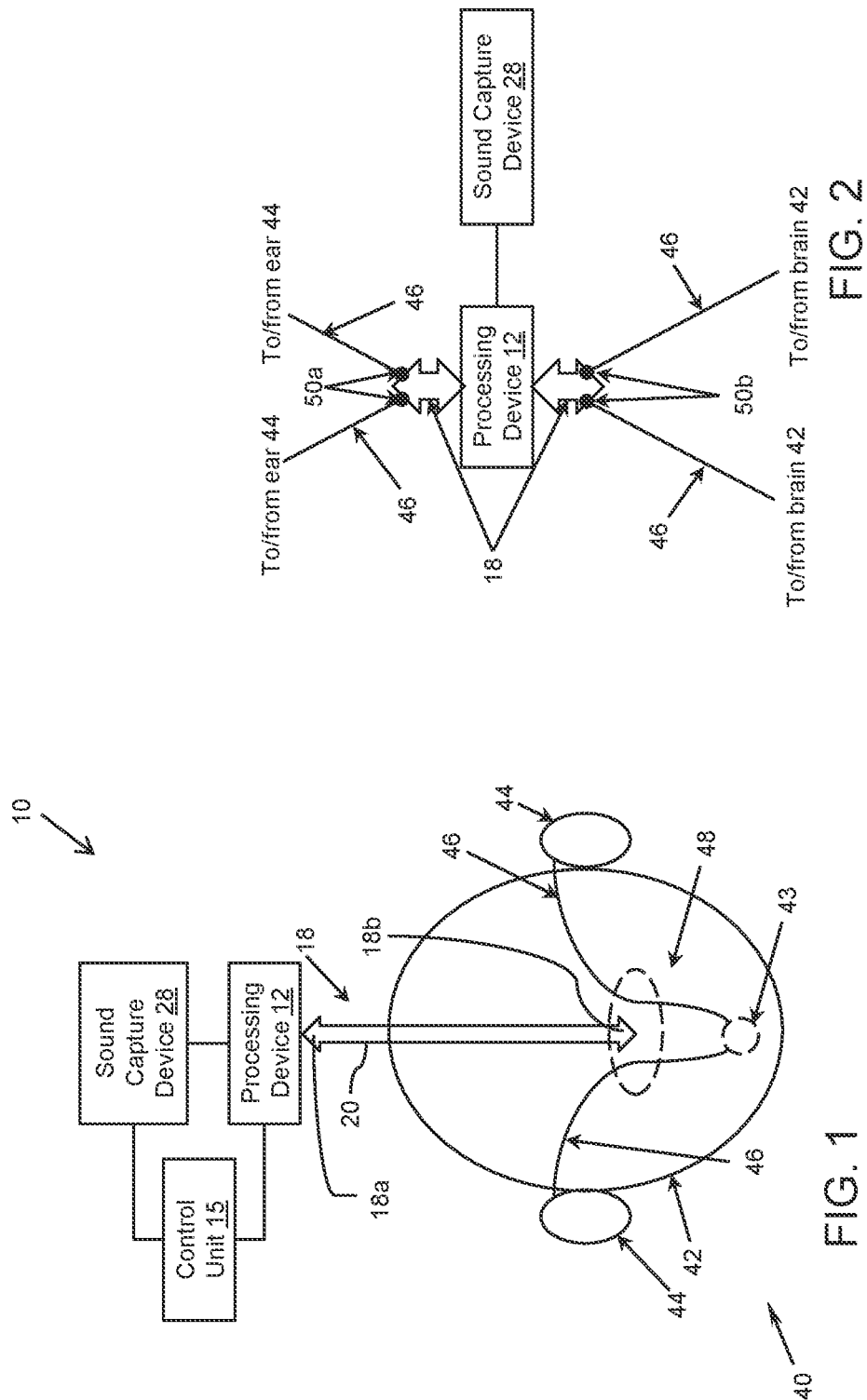

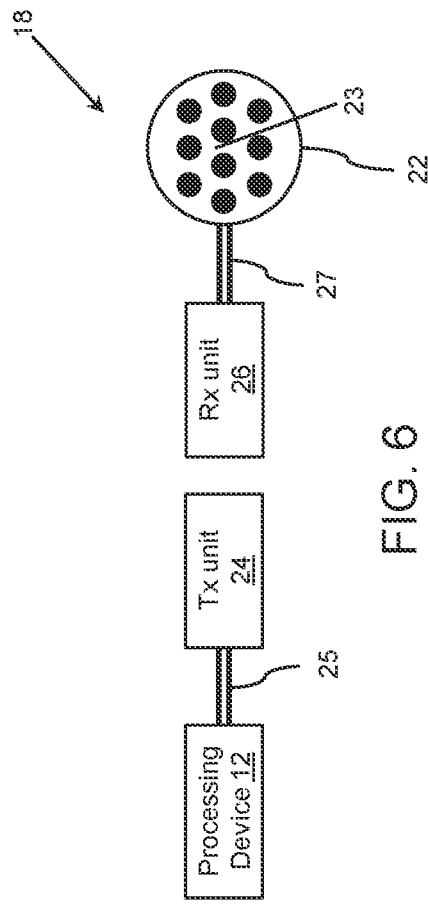
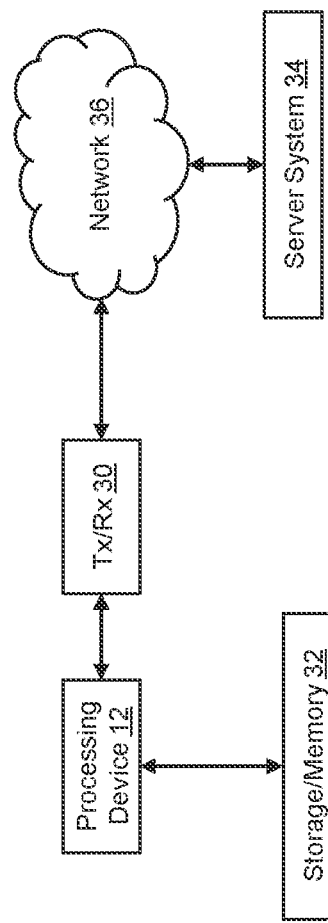
FIG. 5
FIG. 6
FIG. 7

METHODS AND SYSTEMS FOR AUDITORY NERVE SIGNAL CONVERSION

CROSS-REFERENCE TO RELATED APPLICATIONS

This application claims priority from U.S. patent application Ser. No. 17/728,013 filed on 25 Apr. 2022 which claims priority from U.S. Provisional Patent Application No. 63/215,569, filed Jun. 28, 2021, whose disclosure is incorporated by reference in its entirety herein.

TECHNICAL FIELD

The present invention relates to sound perception, and more particularly to the routing of sounds to and from the brain.

BACKGROUND OF THE INVENTION

The human auditory system comprises the ears, the brain, and parts of the nervous system. In general, mechanical waves (vibrations) are detected by the ear and transduced (converted) into nerve pulses that are transmitted to the brain by a nerve or nerves, to be interpreted and perceived by the brain as sound.

SUMMARY OF THE INVENTION

Embodiments of the present invention enable modification of sound (including voice) and related data traversing pathways to the brain by providing methods and systems that obtain signals representative of nerve impulses transmitted by auditory nerves and convert those signals into audio signals (which may be analog or digital signals), and by providing methods and systems that convert audio signals (which may be analog signals or digital signals) into corresponding nerve impulses and provide those nerve impulses to the auditory region of the brain, for example via acoustic nerves for transmission.

According to the teachings of an embodiment of the present invention, there is provided a method for use with an animal subject having a brain that includes an auditory region that is responsible for auditory perception. The method comprises: interfacing a processing device with the auditory region of the brain; receiving, by the processing device, signals associated with nerve impulses transmitted to the auditory region of the brain in response to sound collected by at least one ear of the subject; and processing, by the processing device, the received signals to generate at least one audio signal that is representative of auditory perception, by the subject, of the sound collected by the at least one ear of the subject.

Optionally, the interfacing includes: implanting at least a portion of a machine-subject interface in the subject in association with the auditory region of the brain so as to provide communication between the processing device and the auditory region of the brain.

Optionally, the method further comprises: performing at least one operation on the generated at least one audio signal according to one or more rules.

Optionally, the at least one operation includes: storing data representative of the generated at least one audio signal in a computerized storage device communicatively coupled with the processing device.

Optionally, the at least one operation includes: sending data representative of the generated at least one audio signal to a computerized server system communicatively coupled with the processing device via one or more communication networks.

Optionally, the at least one operation includes: modifying the generated at least one audio signal to produce a modified at least one audio signal.

Optionally, the method further comprises: converting the modified at least one audio signal into one or more nerve impulses; and providing the one or more nerve impulse to the auditory region of the brain so as to augment the auditory perception, by the subject, of the sound collected by the at least one ear of the subject.

Optionally, providing the one or more nerve impulses to the auditory region of the brain includes transmitting the one or more nerve impulses along one or more nerves connected with the auditory region of the brain.

Optionally, the processing the received signals includes: applying to the received signals at least one mapping that maps between nerve impulses and audio signals.

Optionally, the at least one mapping is stored in at least one memory device communicatively coupled with the processing device.

Optionally, the method further comprises: implanting the processing device in the subject.

Optionally, the processing device is external to the subject.

There is also provided according to an embodiment of the teachings of the present invention a system for use with an animal subject having a brain that includes an auditory region that is responsible for auditory perception. The system comprises: a processing device; and a machine-subject interface for interfacing the processing device with the auditory region of the brain. The processing device is configured to: receive signals associated with nerve impulses transmitted to the auditory region of the brain in response to sound collected by at least one ear of the subject, and process the received signals to generate at least one audio signal that is representative of auditory perception, by the subject, of the sound collected by the at least one ear of the subject.

Optionally, at least a portion of the machine-subject interface is configured to be implanted in the subject in association with the auditory region of the brain so as to provide communication between the processing device and the auditory region of the brain.

Optionally, the processing device is further configured to: send data representative of the generated at least one audio signal to one or more of: i) at least one computerized storage device communicatively coupled with the processing device, and ii) at least one remote server system communicatively coupled with the processing device via one or more communication networks.

Optionally, the processing device is further configured to: modify the generated at least one audio signal to produce a modified at least one audio signal.

Optionally, the processing device is further configured to: convert the modified at least one audio signal into one or more nerve impulses, and provide the one or more nerve impulse to the auditory region of the brain so as to augment the auditory perception, by the subject, of the sound collected by the at least one ear of the subject.

Optionally, the processing device is configured to provide the one or more nerve impulses to the auditory region of the brain by transmitting the one or more nerve impulses along one or more nerves connected with the auditory region of the brain.

Optionally, the processing the received signals includes: applying to the received signals at least one mapping that maps between nerve impulses and audio signals.

There is also provided according to an embodiment of the teachings of the present invention a method for use with an animal subject having a brain that includes an auditory region that is responsible for auditory perception. The method comprises: interfacing a processing device with the auditory region of the brain; processing, by the processing device, at least one audio signal representative of at least one sound to convert the at least one audio signal to a sequence of nerve impulses; and selectively providing the sequence of nerve impulses to the auditory region of the brain such that the subject audially perceives the at least one sound.

Optionally, the at least one audio signal is provided to the processing device by at least one of: at least one memory device communicatively coupled with the processing device that stores data representative of the at least one audio signal, or a sound capture device that captures sounds to produce the at least one audio signal.

Optionally, the method further comprises: capturing, by a sound capture device, the at least one sound to produce the at least one audio signal; and providing the at least one audio signal to the processing device.

Optionally, the at least one sound is inaudible to the subject such that when the nerve impulses are provided to the auditory region of the brain the subject perceives silence.

There is also provided according to an embodiment of the teachings of the present invention a system for use with an animal subject having a brain that includes an auditory region that is responsible for auditory perception. The system comprises: a processing device; and a machine-subject interface for interfacing the processing device with the auditory region of the brain. The processing device is configured to: process at least one audio signal representative of at least one sound to convert the at least one audio signal to a sequence of nerve impulses, and selectively provide the sequence of nerve impulses to the auditory region of the brain via the machine-subject interface such that the subject audially perceives the at least one sound.

Optionally, the system further comprises: a sound capture device for capturing the at least one sound to produce the at least one audio signal, and for providing the at least one audio signal to the processing device.

Optionally, the system further comprises: a memory device communicatively coupled with the processing device for storing data representative of one or more audio signals, and the processing device is configured to receive the data from the memory device.

Optionally, the at least one sound is inaudible to the subject such that when the nerve impulses are provided to the auditory region of the brain the subject perceives silence.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings:

FIG. 1 is a schematic representation of a system having a processing device for interfacing with an auditory region of the brain of a subject and for converting nerve impulses into audio signals and vice versa, and having a sound capture device for capturing sound, and a control unit associated with the processing device and the sound capture device, according to an embodiment of the present invention;

FIG. 2 is a schematic representation of an example deployment of the processing device of FIG. 1 in which the processing device interfaces with the auditory region of the brain via implantation at the acoustic nerves, according to an embodiment of the present invention;

FIG. 5 is a schematic representation of an exemplary wired interface that includes an electrode array that can be used for interfacing between the processing device and the auditory region of the brain of the subject, according to an embodiment of the present invention;

FIG. 6 is a schematic representation of an exemplary wireless interface that can be used for interfacing between the processing device and the auditory region of the brain of the subject, showing a transmitter unit connected to the processing device, and an electrode array connected to a receiver unit, according to an embodiment of the present invention;

FIG. 7 is a schematic representation of a system environment in which the processing device according to embodiments of the invention can operate, showing a memory for storing data received from the processing device, and a transceiver unit connected to the processing device for exchanging data with a remote server via a communication network.

DESCRIPTION OF THE PREFERRED EMBODIMENTS

Figure 4:
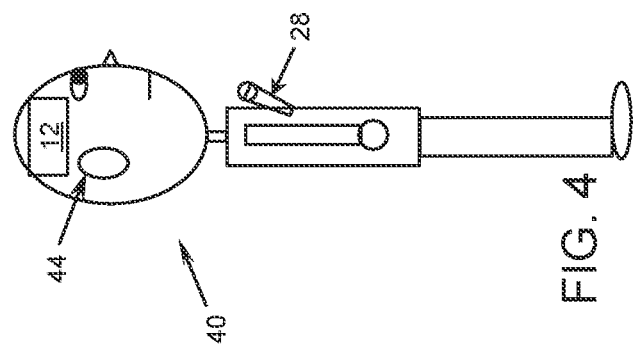
FIG. 4 is a schematic representation of an example deployment of the sound capture device of FIG. 1 as a body-mounted microphone device, according to an embodiment of the present invention.

Embodiments of the present invention provide methods and systems for obtaining signals representative of nerve impulses transmitted by auditory nerves and converting those signals into audio signals (which may be analog or digital signals), and for converting audio signals (which may be analog signals or digital signals) into corresponding nerve impulses and providing those nerve impulses to the auditory region of the brain, for example via acoustic nerves for transmission.

The principles and operation of the methods and systems according to present invention may be better understood with reference to the drawings accompanying the description.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Referring now to the drawings, FIG. 1 is a schematic representation of a system, generally designated 10, according to an embodiment of the present invention. Generally speaking, the system 10 includes a computerized processing device 12 (referred to hereinafter interchangeably as "processing device") for interfacing (communicatively coupling) to a region 43 of the brain 42 of a subject 40 that is responsible for the subject's auditory perception. This region 43 is hereinafter referred to as the "auditory region". In human subjects, as well as many other types of animals (including, for example, canine species, feline species, non-human primate species, rodent species), this auditory region 43 is commonly referred to as the auditory cortex. In human subjects and many other vertebrates, the auditory cortex is a part of the temporal lobe that processes auditory information. In animal species (for example reptile species, bird species, non-mammal marine/aquatic species) that do not have a cerebral cortex or auditory cortex, the term "auditory region" refers to the equivalent portion or portions of the brain that performs auditory processing.

In the illustrated embodiment, the processing device 12 is interfaced with the auditory region 43 via at least one nerve 46, illustrated here as a pair of nerves 46, each of which serves as a pathway between a respective ear 44 and the brain 42. In the context of the present disclosure, the nerve(s) 46 are referred to interchangeably as acoustic nerves or auditory nerves. The term "acoustic nerve" or "auditory nerve" as used herein generally refers to any nerve or nerve segment that can transmit pulses (i.e., nerve impulses), converted from mechanical waves (for example vibrations) detected by the ear or ears 44, to the brain 42 (in particular the auditory region 43 of the brain) so as to be interpreted and perceived by the brain (and hence by the subject) as sound. Typically, for each ear there is an associated acoustic nerve that provides a pathway from the ear to the brain.

In human subjects, the acoustic nerves 46 are the physiological acoustic nerves, which typically include one or more nerves of the vestibulocochlear nerve (also referred to as the auditory vestibular nerve), which includes the cochlear nerve of the vestibular nerve. This may also be true in certain other animal species, including, for example, primate species, canine species, feline species, as well as other vertebrates.

In certain preferred but non-limiting deployment configurations, the processing device 12 is communicatively coupled to the auditory region 43 via either or both of the cochlear nerves (i.e., either a single cochlear nerve that is associated with one of the ears 44, or two cochlear nerves each of which is associated with a respective ear 44).

As will be discussed in further detail below, the processing device 12 is operative to receive signals associated with nerve impulses that carry sound information and that are transmitted to the auditory region 43 of the brain 42. This process of receiving signals by the processing device 12 is generally referred to herein as "collecting nerve impulses" or "collection of nerve impulses". The nerve impulses are typically transmitted by the nerves 46, along the nerve path from the ears 44 to the auditory region 43 of the brain 42, in response to auditory stimulation of the subject's auditory sensory system.

This auditory stimulation can be of several forms, and occurs when the subject (also referred to as a "user") 40 is exposed to sound from one or more audio sources, including natural audio sources and/or electronic audio sources. In general terms, the auditory stimulation occurs when one or both ears 44 collect/sense sound emitted by sources in the subject's environment, for example, people speaking with the subject, music playing in the vicinity of the subject (live instruments and/or singing, or recorded instruments and/or singing played back on an audio output device, e.g., radio, stereo system, etc.), audio output from telephony devices, audio output from video display devices (e.g., televisions, smartphones, etc.), and the like.

The mechanical waves (vibrations) corresponding to the auditory stimulation (sound) are detected/sensed by the ears 44, and are converted into nerve impulses that are transmitted to the auditory region 43 of the brain 42 by the acoustic nerves 46, to be interpreted by the brain 42 as sound. This interpretation of nerve impulses by the brain 42 is referred to herein as "auditory perception".

Parenthetically, in human subjects having a healthy functioning auditory system, the process of sound collection typically includes funneling of the sound vibrations by the outer ear to the eardrum, thereby increasing the sound/vibration pressure in the middle frequency range. The ossicles of the middle-ear then further amplify the pressure (on the order of approximately 20 times), and the vibration/pressure wave form is then converted to nerve impulses in the cochlea of the inner ear.

The processing device 12 is further operative to process the received signals (collected nerve impulses) so as to generate (produce) at least one audio signal (which can be a digital signal or an analog signal) that is representative of the auditory perception (by the subject 40) of the auditory stimulation. In other words, the generated audio signal (or signals) is an analog or digital representation of what the subject 40 hears with his/her ears 44 when the ears 44 are exposed to the auditory stimulation (i.e., when the ears collect the sound). Preferably, a computer-readable and computer-storable version of the generated at least one audio signal can be produced. In embodiments in which the generated at least one audio signal is a digital signal (or digital signals), the digital signal(s) is/are inherently computer-readable and computer-storable. In embodiments in which the generated at least one audio signal is an analog signal (or analog signals), the analog signal(s) can be easily converted to digital form so as to be computer-readable and computer-storable using any number of signal conversion methodologies that are well-known to those of ordinary skill in the art of signal and audio processing.

In certain embodiments, the processing device 12 is further operative to process one or more received audio signals (which can be analog signals or digital sound data, i.e., digital data signals), that is representative of one or more sounds to convert the one or more audio signals into a sequence of nerve impulses (which is defined here as one or more nerve impulses), and to selectively provide or transmit the nerve impulses to the auditory region 43 such that the subject 40 audially perceives the sound(s) as if the subject 40 had heard the sound(s) with his/her ears 44. This audial/auditory perception of the converted audio signal(s) is a faithful representation of what the subject 40 would have perceived had the subject heard the sound(s) with his/her ears 44.

In certain cases, the one or more sounds are sounds that are audible to the subject 40 (i.e., audible sounds or "subject-audible sounds"). Humans can typically detect sounds in a frequency range from about 20 Hz to about 20 kHz, but the auditory region of the brain may be able to process nerve input carrying sound information even outside of this range. Thus, for human subjects, subject-audible sounds include sounds at frequencies in a range between about 20 Hz to about 20 kHz as well as frequencies outside of this range that can still be interpreted by the brain as sound.

In other cases, the one or more sounds are practically/effectively inaudible to the subject and therefore effectively represent silence from the perspective of the subject. These inaudible sounds are sounds that cannot be heard by the subject or cannot be perceived by the subject as sound. This can be sound that is at a very low amplitude (e.g., zero-amplitude) in the time-domain and/or is at frequencies outside of the subject's audible frequency range. For human subjects, for example, inaudible sounds can include sounds at frequencies below 20 Hz or above 20 kHz and/or at frequencies that cannot be interpreted by the brain as sound. In cases where the one or more sounds are inaudible to the subject (i.e., inaudible sounds or "subject-inaudible sounds"), the one or more audio signals that are representative of the one or more sounds effectively represent "silence", and can be represented for example in the time-domain as a finite-time-duration signal of very low amplitude (e.g., zero-amplitude or very close to zero-amplitude) and/or a finite-time-duration signal having only frequency components at frequencies outside of the subject's audible range. Here, when the processing device 12 converts the one or more audio signals (representative of one or more inaudible sounds) to nerve impulses and provides those nerve impulses to the auditory region 43, the subject 40 effectively perceives silence.

In certain embodiments, the processing device 12 is configured to transmit the nerve impulses to the auditory region 43 using the nerves 46 as a signal transmission medium/channel. The processing device 12 may provide (transmit) the nerve impulses to the auditory region 43 via the nerves 46 by inducing nerve transmission of the nerve impulses. In certain embodiments, the processing device 12 converts the audio signals to signals (e.g., electrical signals) that correspond to nerve impulses, and provides the nerve impulses to the nerves 46 by sending the converted signals to a microdevice, for example one or more microelectrodes or microtransducers, implanted in the subject 40 (e.g., at or on a portion of the nerves 46 or the brain 42) that induces transmission of nerve impulses corresponding to the converted signals.

As will be discussed in further detail below, the audio signals that are to be received and processed by the processing device 12 for conversion to nerve impulses are representative of sounds that can be provided from various sources. For example, the audio signals can be representative of sounds captured by a sound capture device (e.g., a microphone) 28 electrically associated with the processing device 12. As another example, the audio signals can be analog representations of digital sound data retrieved from a computerized storage (i.e., memory) linked to, connected to, or otherwise electrically associated with the processing device 12. Accordingly, the processing device 12 is preferably operative to process both analog and digital input.

With continued reference to FIG. 1, the communicative coupling of the processing device 12 to the auditory region 43 can be effectuated by a machine-subject interfacing arrangement 18 (referred to hereinafter interchangeably as "machine-subject interface" or simply "interface") that places the processing device 12 in communication with the auditory region 43 of the brain 42. In certain embodiments, the interface 18 can include two interfacing portions, namely a first interfacing portion 18a and a second interfacing portion 18b. The first interfacing portion 18a, also referred to as electronics interfacing portion 18a, is connected to the processing device 12. The second interfacing portion 18b, also referred to as a subject interfacing portion 18b, can be connected or coupled to the auditory region 43 of the brain 42. The two portions 18a, 18b are interconnected via a linking portion 20 which in certain embodiments can provide a wired connection between the two portions 18a, 18b, and in other embodiments can provide a wireless connection between the two portions 18a, 18b.

Various deployment configurations for achieving communicative coupling of the processing device 12 to the auditory region 43 are contemplated herein, and several example deployment configurations will be described in further detail below. The deployment configurations described herein require some type of implantation, which can employ invasive or semi-invasive techniques. For example, invasive techniques can include implantation by surgically accessing the subject's acoustic nerve(s) and/or auditory region (e.g., auditory cortex) through the subject's skull (i.e., surgically opening the skull). Surgeries performed on the brain, in particular the auditory cortex and the acoustic nerve(s), have become common over the years, and it is asserted that a trained human surgeon and/or a robotic surgeon (such as used by the Neuralink Corporation of San Francisco, USA) can perform the necessary implantation. Before describing several deployment configurations, it is noted that the deployment configurations described herein are exemplary only and represent only a non-exhaustive subset of possible deployment options for the processing device 12. Other deployment options may be possible, as will be apparent to those of skill in the art.

In one example deployment configuration according to certain non-limiting embodiments, the processing device 12 communicates with the acoustic nerves 46 by tapping the acoustic nerves 46 via the interface 18. In such a deployment configuration, the subject interfacing portion 18b can be implanted at or on a segment (section, portion) of the acoustic nerves 46, which in certain non-limiting implementations can be effectuated by first surgically cutting the acoustic nerves 46 to produce cut ends of the acoustic nerves 46, and then connecting the subject interfacing portion 18b to the cut ends. In such a deployment configuration, the processing device 12 preferably remains external to the brain 42 of the subject 40, and most preferably external to the skull so as to be at least partially visible when viewing the subject's head. When the processing device 12 is external to the subject 40, the subject interfacing portion 18b is implanted at or on the acoustic nerves 46 together with either the entirety of the linking portion 20, or a segment of the linking portion 20 that connects to the subject interfacing portion 18b. If only the segment of the linking portion 20 that connects to the subject interfacing portion 18b is implanted, the remaining segment of the linking portion 20, which connects to the electronics interfacing portion 18a, is external to the subject 40. Preferably, the segment of the acoustic nerves 46 at or on which the subject interfacing portion 18b is implanted is in a region (designated as 48 in FIG. 1) where the acoustic nerves 46 (from each of the ears 44) come into proximity with each other.

In another example deployment configuration, the processing device 12 is deployed external to the subject 40, and the subject interfacing portion 18b is implanted at or on the auditory region 43 together with either the entirety of the linking portion 20 or a segment of the linking portion 20 that connects to the subject interfacing portion 18b. If only the segment of the linking portion 20 that connects to the subject interfacing portion 18b is implanted, the remaining segment of the linking portion 20, which connects to the electronics interfacing portion 18a, is external to the subject 40. Such an example deployment configuration is schematically illustrated in FIG. 1.

In yet another example deployment configuration according to certain non-limiting embodiments, the processing device 12 itself, together with the entirety of the interface 18, can be implanted at or on the auditory region 43. In another example deployment configuration according to non-limiting embodiments, the processing device 12 is implanted at or on a segment of the acoustic nerves 46. FIG. 2 schematically illustrates such deployment configuration. Here, the implantation can be effectuated, for example, by first surgically cutting the acoustic nerves 46 to produce cut ends 50a, 50b of the acoustic nerves 46, and then deploying the processing device 12 at the sight of the surgical cut and (surgically) connecting the cut ends 50a, 50b of the acoustic nerves 46 to the processing device 12 via interface 18. In such a deployment configuration, the segment of the acoustic nerves 46 at or on which the processing device 12 is implanted is preferably, but not necessarily, in the region 48 (i.e., where the two acoustic nerves 46 are in proximity to each other), whereby the acoustic nerves 46 are surgically cut (to produce cut ends 50a, 50b) at or within the region 48. It is noted that in embodiments in which the processing device 12 or the interface 18 is implanted at the acoustic nerve 46, care should be taken to ensure that the cut ends 50a, 50b, to which the processing device 12 is interfaced, correspond to the same nerve, otherwise cross-matching may occur where, for example, nerve impulses associated with sound collected by one ear are transmitted to a portion of the auditory region 43 corresponding to the other ear, and vice versa.

As mentioned above, the processing device 12 functions to process received signals that correspond to nerve impulses that are transmitted by one or more of the nerves 46 in response to the ears 44 being exposed to the auditory stimulation. The received signals that are processed by the processing device 12 can be the nerve impulses themselves, or can be representative signals which are produced (i.e., generated) in response to measurement or sampling of the nerve impulses by some type of microdevice, for example a microdevice that has microelectrodes or microtransducers, associated with the processing device 12. The processing device 12 processes the signals (collected nerve impulses) by applying a mapping function or functions (that contain mapping data) to the signals. The mapping function maps between nerve impulses and audio signals, i.e., provides a transformation from nerve impulses to audio signals and vice versa, such that the received signals (that are representative of nerve impulses) are converted (transformed) to audio signals as a result of the application of the mapping function by the processing device 12. This nerve impulse to audio signal mapping function is preferably a one-to-one mapping, and is referred to hereinafter interchangeably as an "impulse-sound mapping". By a one-to-one mapping, it is meant that a single nerve impulse signal maps to a single audio signal, and that a single audio signal maps to a single nerve impulse. In certain embodiments, the mapping between nerve impulses and audio signals also constitutes a mapping between nerve impulses and digital data (since any mapped audio signal can easily be digitized (e.g., sampled and quantized) using audio/signal processing techniques, and vice versa).

Various example methods for generating impulse-sound mapping functions will be described in detail in subsequent sections of the present disclosure.

The mapping function or functions can be stored in a memory device associated with the processing device 12, as will be discussed further below. In certain embodiments, the mapping function(s) can be stored as a data item or data structure, for example in the form of a data table that stores mapping parameters and configurations. In other embodiments, the mapping function(s) can be stored as an equation or a set of equations that provide a functional relationship between audio signals and nerve impulses. The aforementioned formats are exemplary only, and other formats of mapping functions are contemplated herein.

Figure 3:
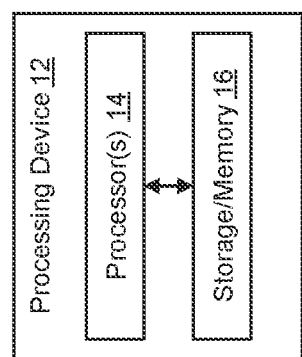
FIG. 3 is a block diagram of an exemplary processing device, according to an embodiment of the present invention.

With continued reference to FIGS. 1 and 2, refer also to FIG. 3, which shows an example block diagram of the processing device 12 according to a non-limiting embodiment of the present invention. The processing device 12 includes one or more processors 14 coupled to a computerized storage medium 16, such as a computerized memory or the like. The one or more processors 14 can be implemented as any number of computerized processors, including, but not limited to, microprocessors, microcontrollers, application-specific integrated circuits (ASICs), field programmable gate arrays (FPGAs), digital signal processors (DSPs), field-programmable logic arrays (FPLAs), and the like. In microprocessor implementations, the microprocessors can be, for example, conventional processors, such as those used in servers, computers, and other computerized devices. For example, the microprocessors may include x86 Processors from AMD and Intel, Xeon® and Pentium® processors from Intel, as well as any combinations thereof. Implementation of the one or more processors 14 as quantum computer processors is also contemplated herein. The aforementioned computerized processors include, or may be in electronic communication with computer readable media, which stores program code or instruction sets that, when executed by the computerized processor, cause the computerized processor to perform actions. Types of computer readable media include, but are not limited to, electronic, optical, magnetic, or other storage or transmission devices capable of providing a computerized processor with computer readable instructions. It is noted that above-mentioned implementations of the one or more processors 14 represent a non-exhaustive list of example implementations. It should be apparent to those of ordinary skill in the art that other implementations of the processing device are contemplated herein, and that processing technologies not described herein or not yet fully developed, including for example biological computing technologies, may be suitable for implementing any of the processing devices discussed herein.

The storage/memory 16 can be any conventional storage media or an application specific storage media, which although shown as a single component for representative purposes, may be multiple components. The storage/memory 16 can be implemented in various ways, including, for example, one or more volatile or non-volatile memory, a flash memory, a read-only memory, a random-access memory, and the like, or any combination thereof. In certain embodiments, the storage/memory 16 can include one or more components for storing and maintaining the impulse-sound mapping, and at least one component configured to store machine executable instructions that can be executed by the one or more processors 16.

In certain embodiments, the processing device 12 is further operative to perform at least one operation on the generated audio signal(s) (which includes the audio signal(s) generated by the processing device 12 by processing nerve impulses via application of the impulse-sound mapping) in accordance with one or more rules or handling criteria. For example, the processing device 12 can be configured to operate on the generated audio signal(s) according to a set of data storage rules or criteria, such that the processing device 12 sends some or all of digital data representative of the generated audio signal(s) to one or more computerized storage/memory devices associated with the processing device 12. Such associated storage/memory devices can include, for example, the storage/memory 16, or other storage/memory devices that are linked or connected to the processing device 12 as will now be discussed.

With additional reference to FIG. 7, examples of other storage/memory devices that can be linked or connected to the processing device 12 include, for example, an external storage/memory 32, and a server system 34 (having a memory). In embodiments in which the processing device 12 sends some or all of digital data representative of the generated audio signal(s) to a server system 34, the server system may be a remote server system, whereby the processing device 12 sends data representative of audio signal (s) to the server system 34 via a communication network 36 (which can be one or more communication networks, such as cellular networks, local area networks, the Internet, etc.). In such embodiments, the processing device 12 can be linked to a transceiver (Tx/Rx) unit 30 that provides a communication/network interface for transmitting/receiving data to/from (i.e., exchanging data with) the network 36.

In another non-limiting example, the processing device 12 can be configured to operate on the generated audio signal(s) according to a set of signal modification or manipulation rules or criteria to produce a modified audio signal or modified audio signals. For example, the processing device 12 can modify the generated audio signal(s) by adding additional sounds (either from the sound capture device 28 or from a memory associated with the processing device 12, e.g., the storage/memory 16, external storage/memory 32, server system 34), and/or changing or deleting data elements (e.g., bits) of a digital version of the generated audio signal(s), and/or adjusting audio parameters of the audio signal(s), including, for example, volume, pitch, tones, etc. For example, the processing device 12 can modify the audio signal to increases or decrease the volume associated with the sound from which the audio signal was generated. As another example, the processing device 12 can modify the audio signal to change one or more frequencies (tones) of the sound. As an additional example, the processing device 12 can modify the generated audio signal by performing noise cancellation or interference reduction signal processing on the generated audio signal, thereby reducing background noise or interference. In a further example, the processing device 12 can modify the generated audio signal by performing cancellation processing on the audio generated signal in order to provide the subject with the perception of silence. For example, the processing device 12 can combine the generated audio signal with a negative displacement version of the generated audio signal to induce destructive interference such that the two signals combine together to effectively cancel each other out, thereby resulting a finite-time-duration signal of zero-amplitude (or very close to zero-amplitude).

In certain embodiments, the processing device 12 can then convert the modified audio signal(s) back to nerve impulses (using the impulse-sound mapping), and transmit those nerve impulses to the brain 42 via the acoustic nerve 46. In certain embodiments, this can be used to augment perceived sound by the subject 40, whereby the brain 42 interprets the received nerve impulses as the original sound sensed by the ears 44 augmented with the additional sound. For example, a person listening to a piece of music can have the musical sounds sensed by his/her ears 44 augmented to include voice-over (for example voice-over digital sound data stored in and uploaded from memory such as the storage/memory 16) discussing various aspects of the musical piece (e.g., composer/singer information, inspiration for the piece, historical context, etc.). In other embodiments, for example when the processing device 12 modifies the generated audio signal to induce destructive interference to produce a modified audio signal that is a zero-amplitude signal, the modified audio signal that is converted into nerve impulses is representative of inaudible sound such that when the nerve impulses that are generated from the modified audio signal are provided to the auditory region 43 of the brain, the subject perceives the nerve impulses as silence.

The modified audio signal(s) can also be stored in digital form in memory (e.g., storage/memory 16 and/or external storage/memory 32 and/or server system 34).

In certain embodiments, the processing device 12 is further operative to convert audio signals (which can be analog signals or digital sound data signals) to nerve impulses (or electrical signals that represent nerve impulses) to be transmitted by the nerves 46. The conversion of audio signals to nerve impulses is effectuated by applying the impulse-sound mapping function discussed above. Since each subject may perceive or interpret sound differently, the mapping for each subject may be a subject-specific mapping (i.e., the mapping for one subject may be different from the mapping for another subject). However, regardless of the specificity of a given impulse-sound mapping, the mapping is preferably such that the nerve impulses converted from audio signals using the impulse-sound mapping function(s) faithfully creates auditory perception of the true sound for the subject 40.

The audio signals that are to be converted to nerve impulses can be, for example: i) analog audio signals obtained from an external source, such as a sound capture device (e.g., the sound capture device 28 in FIGS. 1 and 2), that captures sound and produces analog audio signals from the captured sound and provides the analog audio signals to the processing device 12 for processing, ii) digital sound data obtained from an external source, such as a sound capture device, that captures analog sound and converts the analog sound to digital sound data or provides the captured analog sound to the processing device 12 for digitization (i.e., conversion to digital sound data), iii) digital sound data obtained from an external source such as a memory that stores sounds in digital form, iv) audio signal(s) generated by the processing device 12 from collected nerve impulses, v) the modified audio signal(s) resultant from the modification applied by the processing device 12 discussed above, vi) any other source of audio signal and/or any combination of i), ii), iii), iv), and v) above.

In embodiments in which the sound capture device 28 provides audio signals as digital signals (i.e., digital data) to the processing device 12, the digital signals can be provided in any suitable data format or standard, including, lossy formats such as, for example, Moving Picture Experts Group (MPEG)-1 Audio Layer III (commonly known as MP3), Advanced Audio Coding (AAC), and lossless or uncompressed formats such as, for example, Free Lossless Audio Codec (FLAC), Waveform Audio File (WAV), and the like. The processing device 12 may, in certain embodiments, convert the digital signal(s) to analog form and then apply the impulse-sound mapping to the analog signal(s).

In embodiments in which the sound capture device 28 provides analog audio signals representative of captured sound to the processing device 12, the processing device 12 can be further configured to the process the analog signals to convert the analog signals to digital data that is compliant with any suitable sound data format or standard, such as any of the formats and standards listed above.

Furthermore, digital data (representative of audio signals) can be transmitted to or from the processing device 12 using any suitable transmission format or standard, including, for example, Real Time Streaming Protocol (RTSP), Transmission Control Protocol (TCP), User Datagram Protocol (UDP), and the like, as well as any other commonly used standards for data transmission, including wireless data transmission standards such as cellular standards (e.g., 3G, 4G/LTE, 5G, etc.), wireless communication standards (e.g., Wi-Fi, Bluetooth, etc.) and the like, and wired communication standards.

In another non-limiting example, the processing device 12 can be configured to operate on the generated audio signal(s) according to a set of playback rules or criteria. For example, the processing device 12 can be configured to provide the generated audio signal(s) in digital form to a digital audio playback device (e.g., MP3, digital stereo, etc.) connected or linked to the processing device 12 such that the audio playback device audibly plays sound represented by the generated audio signal(s). The processing device 12 can transmit or send the digital data to such an audio playback device using any suitable audio transmission format or standard, or any commonly used standards for data transmission, including any of the formats and standards discussed above. Alternatively, the processing device 12 can be configured to provide the generated audio signal(s) in analog form to an analog audio playback device.

In the exemplary embodiments illustrated in FIGS. 1 and 2, the system 10 further includes the sound capture device 28 (referred to interchangeably herein an "audio capture device") that is operative to capture sounds from an environment, including the environment in which the subject 40 is currently located or an environment that is remote from the subject's current location. In certain embodiments, the sound capture device 28 can be used as bionic/electronic ears of the subject 40 for allowing the subject 40 to hear sounds captured by the sound capture device 28 (which may be of particular advantage for subject's that suffer from hearing loss), or for augmenting the subject's natural audial/auditory perception of an environment with sounds captured by the sound capture device 28.

In certain embodiments, the sound capture device 28 captures sound to produce one or more analog audio signals and converts the one or more analog audio signals to digital data and sends the digital data to the processing device 12. The processing device 12 may directly process the digital data using a digital version of the impulse-sound mapping, or may convert the digital data to analog form and then apply the impulse-sound mapping. In other embodiments, the sound capture device 28 provides the audio analog signals to the processing device 12 for processing. The processing device may process the analog audio signals using the impulse-sound mapping, or may digitize the analog audio signals to produce digital data and then process the digital data using a digital version of the impulse-sound mapping.

It is noted that conversion of analog audio signals to digital form is preferably performed (by the sound capture device 28 or by the processing device 12) in accordance with any suitable format or standard, including any of the standards discussed above, which rely on signal conversion methodologies that are well-known to those of ordinary skill in the art of signal and audio processing. Furthermore, in certain embodiments the sound capture device 28 can transmit digital data to the processing device 12 using any suitable transmission format or standard, or any commonly used standards for data transmission, including any of the formats and standards discussed above.

With continued reference to FIGS. 1-3, refer also to FIG. 4, which illustrates a non-limiting deployment configuration of the sound capture device 28. Here, the sound capture device 28 is mounted (preferably indirectly) to a subject 40, for example on an item of clothing (e.g., a shirt, blouse, etc.) covering the upper portion of the subject's torso (e.g., chest). This is merely illustrative, and the sound capture device 28 can easily be mounted or attached (preferably indirectly) to another portion of the subject's body, such as other portions of the torso (e.g., back, mid-section, waist), arms, legs, head, and the like. Alternatively, the sound capture device 28 can carried by, or otherwise associated with, the subject. For example, the subject can simply hold the sound capture device in his/her hand or can keep the sound capture device in a pocket of an item of clothing that he/she is wearing. In one non-limiting example, a mobile communication device (e.g., cellular phone, smartphone, tablet, etc.) of the subject can provide sound capture functionality, for example via one or more software applications executed by a processor of the mobile communication device. In a simple example, a smartphone having audio capture (e.g., recording) capability can function as the sound capture device, and can be connected to the processing device 12 via a software application executed by the smartphone.

In addition, although illustrated as a single device, more than one sound capture device 28 can be deployed in order to capture sounds emanating from different directions or locations relative to the spatial positioning or orientation of the subject 40. For example, one microphone can be deployed with a first spatial orientation to capture sounds emanating from a first direction or region, and another microphone can be deployed with a second spatial orientation (different from the first spatial orientation) to capture sounds emanating from a second direction or region that is different from (but possibly partially overlapping with) the first direction or region. The processing device 12 can provide the nerve impulses (corresponding to the different sounds) to the auditory region 43 individually or in combination (preferably according to subject selected preferences). For example, the subject may select that the processing device 12 provide all of the nerve impulses corresponding to the different sounds to the auditory region 43 together, such that all of the sounds are heard together by the subject. In another example, the subject may select that the processing device 12 provide the nerve impulses corresponding to the different sounds to the auditory region 43 sequentially, such that individual sounds are heard separately by the subject.

In other deployment configurations, the sound capture device 28 can be remote from the subject 40, for example the subject 40 can be positioned in an environment in a first geographic location, and the sound capture device 28 can be located in a second geographic location that is remote from the first geographic location. In such configurations, the sound capture device 28 preferably includes or is connected to a transceiver device that is operative to transmit the audio signals (captured by the sound capture device 28) to a transceiver (e.g., Tx/Rx unit 30 of FIG. 7) connected to the processing device 12 via one or more communication networks.

As alluded to above, in certain embodiments, the sound capture device 28 can be used together with the processing device 12 to provide the subject 40 with electronic ears. In situations in which the subject 40 has a healthy functioning auditory system, the subject can optionally inhibit their natural hearing (for example by wearing noise-cancelling headphones) while the system 10 functions as electronic ears. In general, the sound capture device 28 captures sound from an environment and provides the audio signal(s) representative of the captured sound(s) (in analog or digital form) to the processing device 12 for nerve impulse conversion. The sound captured by the sound capture device 28 can be the same sounds the subject would otherwise hear if the subject's hearing were not inhibited, or can be different sounds (for example if the subject and the sound capture device 28 are in different geographic locations).

The processing device 12 converts audio signals (provided by the sound capture device 28) to nerve impulse signals using the impulse-sound mapping. The processing device 12 then transmits the nerve impulses to the brain 42 via the acoustic nerves 46, where the brain 42 interprets the received nerve impulses as hearing/sound such that the subject audially perceives the sound captured by the microphone 28 as if the subject were hearing the sounds him/herself (the mapping is preferably such that the audial/auditory perception is a faithful representation of the sound). In other embodiments, digital sound data stored in memory that is electrically associated with the processing device 12 (e.g., storage/memory 16 and/or external storage/memory 32 and/or server system 34) can be uploaded to the processing device 12. The processing device 12 can process the uploaded sound data using the impulse-sound mapping in order to convert the sound data to nerve impulses. The processing device 12 can then transmit the nerve impulses to the brain 42 such that the nerve impulses are interpreted by the brain 42 as hearing/sound. For example, a series of sounds, such as a piece of music or an audio book, can be stored in such a memory, and uploaded/streamed to the subject.

According to certain embodiments of the present invention, the system 10 can be used to provide a mixed-reality experience to the subject 40 by fusing environmental sounds that the subject 40 can hear with one or more additional sounds. In one set of non-limiting examples, the fusing can be performed when the subject 40 is listening to (i.e., hears) real-world sounds with his/her ears 44. In a first example, the fusing can be accomplished by using the processing device 12 to convert nerve impulses, generated by the subject 40 in response to hearing the real-world sounds, to one or more audio signals (preferably in digital form). The processing device 12 can then modify the audio signal(s) to include parts of sounds captured by the sound capture device 28. The processing device 12 can then convert the modified audio signal(s) to nerve impulses and provide those nerve impulses to the auditory region 43, such that the subject perceives the environmental sounds and the parts of the sound capture device sounds as a single sound. In a second example, the fusing can be accomplished by using the processing device 12 to convert audio signals (obtained, for example, from the sound capture device 28 or a computer memory device) to nerve impulses (or electrical signals representative of nerve impulses), and to provide those nerve impulses to the acoustic nerves 46 such that the nerve impulses are transmitted to the auditory region 43. The brain 42 then combines the sound information (carried by the nerve impulses generated by the processing device 12) with the sound information (carried by the nerve impulses generated by the subject 40 in response to hearing the real-world sounds) as a single sound.

In another non-limiting example, the sound capture device 28 can be used to capture sounds to produce audio signals, and the processing device 12 can modify the audio signals (generated by the sound capture device 28) to include additional audio signals (for example from memory or from another audio source) representative of a different sound. The processing device 12 can optionally combine (e.g., via superposition) the modified audio signals with audio signals generated from nerve impulse (generated by the subject 40 in response to hearing real-world sounds) and then convert the combined signal to nerve impulses and provide those nerve impulses to the brain 42 (for example via the acoustic nerves 46), whereupon the brain 42 interprets the nerve impulses as a single sound.

Parenthetically, it is noted herein that the nerve impulses which are converted, by the processing device 12, from audio signals should be provided to the auditory region 43 of the subject at an appropriate rate so that the subject has an opportunity to appropriately perceive the corresponding sound. Specifically, if the nerve impulses are provided to the auditory region 43 too quickly, the subject may not be able to perceive the corresponding sound (i.e., the sounds may change too quickly for the subject to notice, which may become disorienting to the subject). Likewise, if the nerve impulses are provided to the auditory region 43 too slowly, the subject may perceive a corresponding sound that is no longer relevant to the real-world environment that the subject is listening to or observing with his/her ears or which no longer matches or synchronizes with corresponding actions in the real-world environment that are viewed by the eyes of the subject (similar to how the subject perceives sound when exposed to the Doppler effect). Thus, the processing device 12 preferably controls the timing at which any such nerve impulses are provided to the auditory region 43, to ensure that the subject is able to appropriately perceive the corresponding sound. The rate at which the nerve impulses (converted from audio signals) are provided to the auditory region 43 may be user (i.e., subject) specific, since some users may be able to perceive sounds at a faster rate or slower rate than other users. Thus, the control of the timing (rate) at which nerve impulses are provided to the auditory region 43 is preferably adjustable by the user of the system 10.

In the electronic ears and/or the mixed-reality embodiments described above, the processing device 12 may be further operative to convert the nerve impulses to audio signal(s) and to perform at least one operation on the audio signal(s) according to one or more rules or criteria. For example, the processing device 12 can be configured to operate on the audio signal(s) according to a set of data storage rules or criteria, and/or be configured to operate on the audio signal(s) according to a set of signal modification or manipulation rules or criteria, similar to as discussed above.

It is noted herein that the processing device 12 can employ various techniques for obtaining nerve impulses (and their representative electrical signals) from the nerves 46 of the subject and for providing nerve impulses (converted from audio signals) to the nerves 46 to induce transmission (by the nerves 46) of the provided nerve impulses. Such techniques may typically rely on employing microdevices, such as microelectrodes or microtransducers, for measuring (receiving) nerve impulses and producing electrical signals in response thereto, and/or for stimulating the nerves 46 with electrical signals so as to induce transmission of the corresponding nerve impulses. Various entities have conducted research, development, and experimentation on connection and interfacing of computer processing devices to the brain, tissue, and nerves via implantation or other invasive or semi-invasive means. One example of such research can be found in a publication by the University of Luxembourg in 2019 entitled "CONNECT—Developing nervous system-on-a-chip" (available at https://wwwfr.uni.lu/lcsb/research/developmental_and_cellular_biology/news/connect_developing_nervous_system_on_a_chip), which describes culturing individual nervous system components and connecting the components in a microfluid chip (integrated circuit).

Examples of research and experimentation in the field of brain-machine interfacing is described in an article published in Procedia Computer Science in 2011, entitled "Brain-Chip Interfaces: The Present and The Future" by Stefano Vassanelli at the NeuroChip Laboratory of the University of Padova in Italy. In one example, computerized processing devices are interfaced to neurons with metal microelectrodes or oxide-insulated electrical microtransducers (e.g., electrolyte-oxide-semiconductor field-effect transistors (EOSFETs) or Electrolyte-Oxide-Semiconductor-Capacitors (EOSCs)) to record (i.e., measure) or stimulate neuron electrical activity. In another example, large-scale high-resolution recordings (i.e., measurements) from individual neurons are obtained using a processing device that either employs or is coupled to a microchip featuring a large Multi-Transistor-Array (MTA). In yet a further example, a microchip featuring a large MTA is used to interface with the cells in vitro by deploying the MTA in contact with brain tissue, where the signals corresponding to nerve impulses are, in one example, in the form of local-field-potentials (LFPs).

An example of a brain-machine interface device is the Neuralink device, developed by Neuralink Corporation of San Francisco, USA. The Neuralink device includes an ASIC that digitizes information obtained from neurons via microelectrodes.

Bearing the above in mind, the following paragraphs provide a high-level description of an interface 18 that can be used for connecting/interfacing the processing device 12 to the subject 40 so as to provide a machine-brain interface, according to non-limiting example embodiments of the present invention.

With continued reference to FIGS. 1-4, refer also to FIG. 5, which illustrates a schematic representation of the interface 18 according to a non-limiting embodiment of the invention. Here, the subject interfacing portion 18b includes an electrode array 22, having a plurality of electrodes 23, that is deployed at or on the acoustic nerves 46. The electrodes 23 are preferably microelectrodes, such as EOSFETs or EOSCs. In embodiments in which the processing device 12 is operative to convert nerve impulses to audio signals, the electrode array 22 is operative to measure nerve impulses transmitted by the acoustic nerves 46 and produce (in response to the measurements) electrical signals associated with (and representative of) the nerve impulses, and provide those signals to the processing device 12 in order to enable the processing device 12 to collect the nerve impulses and process the electrical signals that correspond to (i.e., represent) the nerve impulses. In the illustrated embodiment, the linking portion 20 can be implemented as a wire or cable that provides a physical transmission medium along which the electrical signal can propagate to the processing device 12. In certain embodiments, the interface 18 can employ a transducer (preferably a microtransducer as discussed above) as part of the subject interfacing portion 18b, either instead of or in addition to electrode array 22. The transducer can be used together with the processing device 12 for conversion of nerve impulses to audio signal(s). For example, the transducer can generate electrical signals in response to receiving (measuring) nerve impulses transmitted by the acoustic nerves 46. The generated electrical signals correspond to (i.e., are representative of) the nerve impulses, and are provided to the processing device 12 for processing using the impulse-sound mapping.

In embodiments in which the processing device 12 is operative to convert the audio signals to nerve impulses and transmit the nerve impulses to the brain 42 via the acoustic nerves 46 such that the nerve impulses are interpreted by the brain 42 as hearing/sound, the transmission of the nerve impulses may be effectuated by stimulation of one or more neurons of the acoustic nerves 46 by a microdevice, e.g., the electrode array 22 (or a transducer). Generally speaking, in such embodiments the processing device 12 can convert (using the impulse-sound mapping) audio signals to nerve impulses (or electrical signals that represent nerve impulses) that are to be transmitted by the nerves 46. The processing device 12 then provides the nerve impulses to the nerves 46 to induce nerve transmission of the nerve impulses (or provides the electrical impulses to the nerves 46 to induce nerve transmission of the nerve impulses represented by the electrical impulses). In certain embodiments, the inducing of nerve transmission can be effectuated by the processing device 12 providing electrical signals to the electrode array 22 (or a transducer), which stimulates the neurons of the acoustic nerves 46 in accordance with the electrical signals so as to induce transmission of corresponding nerve impulses.

FIG. 6 illustrates another embodiment that employs wireless signal transmission for providing electrical signals to the microdevice, represented here as electrode array 22. Here, the processing device 12 is connected to a transmitter (Tx) unit 24 via a wire or cable 25, and the electrode array 22 is connected to a receiver (Rx) unit 26 via a wire or cable 27. The Tx unit 24 includes transmitter circuitry and components for transmitting the electrical signals produced by the processing device 12 via a wireless interface to the Rx unit 26. The Rx unit 26 includes receiver circuitry and components which receive the electrical signals, and provide the received signals to the electrode array 22 which stimulate the nerves 46 to induce the nerves 46 to transmit nerve impulses corresponding to the electrical signals.

In certain embodiments, the wireless transmission can be RF signal transmission. In such embodiments, the transmitter circuitry and components of the Tx unit 24 can include, for example, signal transmission electronics and components such as one or more antenna, digital-to-analog conversion circuitry, signal modulators, filters, amplifiers, etc., and the receiver circuitry and components of the Rx unit 26 can include, for example, signal reception electronics and components such as one or more antennas, filters, amplifiers, demodulators, etc. In other embodiments, the wireless transmission can be indictive signal transmission whereby the Tx unit 24 and the Rx unit 26 are operative to transmit and receive, respectively, using inductive signal transmission means. In such embodiments, for example, the Tx unit 24 can include inductive coils, and the Rx unit 26 can include an induction receiver.

It is noted that in certain embodiments, the interfacing arrangement 18 can include multiple interfaces. For example, a first interface can be used to effectuate conversion of audio signals to nerve impulses. The first interface can employ an electrode array 22 or microtransducers (implemented, for example, as EOSCs) connected or linked to the processing device 12 via a wired connection (for example as shown in FIG. 5) or wireless connection (for example as shown in FIG. 6). A second interface can be used to effectuate conversion of nerve impulses to audio signals. The second interface can employ an electrode array 22 and/or microtransducers (implemented, for example, as EOSFETs) connected or linked to the processing device 12 via a wired connection (for example as shown in FIG. 5).

The following paragraphs describe various methods and techniques for generating impulse-sound mapping functions, as well as exemplary processes for applying the mapping functions. By employing an impulse-sound mapping, the system 10 according to embodiments of the present invention can convert sounds perceived by the ears 44 (i.e., hearing) into audio signals (in the form of analog signals and/or digital sound data), and can convert analog audio signals and/or digital sound data (for example obtained from sound capture devices (e.g., microphones), computerized devices (e.g., computer memory, digital audio players, digital video players, and the like) into nerve impulses that can be routed to the brain to induce audial/auditory perception and/or augment hearing.

According to certain embodiments, generation of the impulse-sound mapping can be aided by machine learning (ML) or neural networks (NN) algorithms. For example, the processing device 12 can employ one or more ML or NN algorithms to learn the signal format of nerve impulses (in response to auditory stimulation of the ears 44), and to determine the mapping by comparing the nerve impulse format to audio signals, including, for example, digital data stored in a memory associated with the processing device 12 and/or analog audio signals generated by the sound capture device 28 in response to capturing sound.

By way of one non-limiting example, an audio sample signal can be generated, which is an amplitude varying signal over some fixed time duration. The audio sample signal is an analog signal that may consist of multiple frequency components corresponding to various sounds (frequency tones), which can be isolated using frequency analysis techniques, e.g., Fourier analysis, including Fast Fourier Transform (FFT). Sound vibrations from the audio sample signal are captured by the ears 44 and the processing device 12 collects the nerve impulses sent from the ears 44 to the auditory region 43 of the brain 42 (along the acoustic nerves 46) in response to hearing the sample audio. Subsequently, the same audio sample can be played such that the sample is captured by a sound capture device (e.g., the sound capture device 28) connected to the processing device 12. The processing device 12 collects the audio signals transmitted from the sound capture device to the processing device 12, and analyzes/processes the audio sample signal. The analysis/processing can include, for example, digitization (sampling and quantization) and/or frequency analysis (e.g., FFT). Subsequently, a small change to one or more of the signal characteristics can be made to the audio sample signal, for example by changing one or more of the frequency components or an amplitude value of the audio sample signal, to produce a new audio sample signal. The sound vibration from the new audio sample signal is captured by the ears 44, and the processing device 12 collects the nerve impulses sent from the ears 44 to the auditory region 43 of the brain 42 (along the acoustic nerves 46) in response to hearing the new audio sample signal. The same new audio sample signal can then be played such that the sample is captured by the sound capture device, and the processing device 12 collects the audio signals transmitted from the sound capture device to the processing device 12. The processing device 12 analyzes/processes the new audio sample signal (e.g., via digitization and/or FFT). This process can continue by changing the characteristics of the audio sample signal either individually one at a time (e.g., changing a single frequency component, or changing an instantaneous amplitude value), or in incrementally larger groups of signal characteristics (e.g., changing multiple frequency components and/or changing multiple instantaneous amplitude values). For each change to the audio sample signal, the change in the nerve impulse from the ears 44 (compared to the previous sample) is compared with the change in the audio signals collected by the processing device 12 from the sound capture device. This process can continue until each nerve impulse from the ear 44 can be matched to a corresponding audio signal component (e.g., sound) transmitted by the sound capture device. This matching between each nerve impulse and a corresponding audio signal component constitutes a mapping between nerve impulses and sounds (i.e., an impulse-sound mapping). Note that the changes to the audio sample signal should preferably cover multiple combinations of sounds (frequency tones), more preferably sounds over any given range of amplitudes and/or frequencies.

Typically the process for generating the impulse-sound mapping only needs to be performed once, and the generated impulse-sound mapping can then be used thereafter. However, alteration and/or adjustment and/or refinement of the mapping can be performed if needed or wanted.

Referring now again to FIG. 1, in preferred embodiments the system 10 also includes a control unit 15 that is connected or linked (electronically) to the processing device 12 and the sound capture device 28, and is configured to control the operation of the processing device 12 and the sound capture device 28. The control unit 15 preferably includes one or more user input interfaces (e.g., touchscreen, pushbuttons, dials, knobs, electronics keypad, (electronic) keyboard, etc.) that allow the user to provide input to the control unit 15. In response to receiving input via the user input interface, the control unit 15 is preferably operative to provide control commands to the processing device 12 and/or the sound capture device 28 which control or change the operation of the processing device 12 and/or the sound capture device 28.

In one example, the control unit 15 allows the user to define the rules or handling criteria that determine the at least one operation performed on generated audio signal(s) by the processing device 12, as well as to select the handling rule and/or change from the selected rule to another rule. For example, the user can define a set of rules according to which the processing device 12 operates. As an additional example, the user can select an existing rule/set of rules (e.g., data storage rules, signal modification rules, playback rules) or a newly defined rule/set of rules such that the processing device 12 operates according to the selected rule(s) (e.g., a set of data storage rules (criteria), a set of signal modification (manipulation) rules, or a set of playback rules (criteria)). In addition, the user can select, via the control unit 15, parameters related to the defined rules. For example, if the user selects that the processing device 12 is to operate according to a set of signal modification (manipulation) rules, the user can select how the generated audio signal(s) is to be modified, including selecting any additional sounds that are to be used to modify generated audio signal(s). These additional sounds can be received from various sources, including, for example, a computer memory associated with the processing device 12 that stores sounds in digital form, an audio capture or input device such as a microphone or audio player, and the like.

As another example, if the user selects that the processing device 12 is to operate according to a set of data storage rules, the user can select the memory device (e.g., storage/memory 16, external storage/memory 32, server system 34) for storing data that is representative of the generated audio signal(s), and may also select which portions (segments or sub-samples) of the data are to be stored on which memory device (e.g., the user can select some of the data to be stored locally in storage/memory 16, and select other parts of the data to be stored remotely at server system 34).

The control unit 15 also preferably allows the user to select audio signal(s) that is/are to be converted to nerve impulses by the processing device 12. The selection can be applied via a menu that is part of the user input interface of the control unit 15. The menu may include a list of digital audio tracks or sounds that are stored in a memory associated with the processing device 12. In addition, the control unit 15 preferably allows the user to adjust and set the rate at which nerve impulses, converted from audio signals by the processing device 12, are provided to the auditory region 43. The rate setting can be applied via the user input interface of the control unit 15.

In certain preferred embodiments, the control unit 15 provides selective switching between different operational modes of the system 10 in response to user input. For example, the control unit 15 can selectively switch the sound capture device 28 on or off, and/or actuate the sound capture device 28 to capture sounds, and/or actuate the processing device 12 to retrieve audio signal(s) from the sound capture device 28 or a memory (e.g., storage/memory 16, storage/memory 32, a server system 34). As such, the control unit 15 can enable the user to control if and when sounds (e.g., digital audio signals) from a memory (e.g., storage/memory 16, storage/memory 32, a server system 34) or captured by the sound captured device 28 are converted to nerve impulses, and/or if and when such converted nerve impulses are transmitted via the nerves 46. In this way, the user can control if and when the user perceives sounds, akin to selectively switching electronic/bionic ears on and off.

In addition, the control unit 15 is preferably operative to actuate the processing device 12 to adjust audio parameters (including volume, pitch, speed, tones) of captured sounds that are stored in a memory associated with the processing device 12, and/or adjust sound parameters of audio signal(s) that is/are to be converted to nerve impulses. This feature may be of particular advantage for enhancing and/or cleaning up noisy audio signals. For example, the subject 40 can employ the control unit 15 to actuate the processing device 12 to apply one or more audio filters to remove or reduce interference or noise. As another example, the subject 40 may choose to increase the volume and/or slow or speedup the playback rate of digital audio data that is stored in memory or received from the sound captured device 28. For example, the subject 40 can use the control unit 15 to actuate the processing device 12 to amplify or attenuate the audio signal(s) and/or to control playback timing.

The control unit 15 is a computerized control unit that includes one or more computer processors coupled to a computerized storage medium (e.g., memory). The one or more processors can be implemented as any number of computerized processors, including, but not limited to, as microprocessors, microcontrollers, ASICs, FPGAs, DSPs, FPLAs, state machines, bioprocessors, and the like. In microprocessor implementations, the microprocessors can be, for example, conventional processors, such as those used in servers, computers, and other computerized devices. For example, the microprocessors may include x86 Processors from AMD and Intel, Xeon® and Pentium® processors from Intel. The aforementioned computerized processors include, or may be in electronic communication with computer readable media, which stores program code or instruction sets that, when executed by the computerized processor, cause the computerized processor to perform actions. Types of computer readable media include, but are not limited to, electronic, optical, magnetic, or other storage or transmission devices capable of providing a computerized processor with computer readable instructions. The storage/memory of the control unit 15 can be any conventional storage media and can be implemented in various ways, including, for example, one or more volatile or non-volatile memory, a flash memory, a read-only memory, a random-access memory, and the like, or any combination thereof. In certain embodiments, the storage/memory of the control unit 15 can store machine executable instructions that can be executed by the one or more processors of the control unit 15.

In certain embodiments, the processing device 12 and the control unit 15 share one or more common processors, such that the processing device 12 is operative to perform both processing and control functionality. In other sometimes more preferable embodiments, the control unit 15 and the processing device 12 are separate electronic devices that are electronically connected via a wired or wireless connection. In such embodiments, the control unit 15 can be implemented as a user computer device, which includes, for example, mobile computing devices including but not limited to laptops, smartphones, and tablets, and stationary computing devices including but not limited to desktop computers.

In other embodiments, the control unit 15 is implemented via application software executed on an electronic device, such as a mobile communication device (e.g., smartphone, tablet, etc.) or computer device (e.g., laptop, desktop, etc.). In embodiments in which the control unit 15 is implemented on a smartphone, tablet, laptop, etc., the software application can provide a user input interface. In certain embodiments, the control unit 15 provides control via direct wired connection or indirect wireless connection to the processing device 12.

Although the embodiments described thus far have pertained to using a single processing device 12 that is operative to convert nerve impulses, that are received in response to auditory stimulation of the ears, to audio signal(s), and is further operative to convert audio signal(s) to nerve impulses and to provide those nerve impulses to the auditory region 43, other embodiments are possible in which the tasks of conversion of nerve impulses to audio signal(s) and the conversion of audio signal(s) to nerve impulses are subdivided amongst two (or more) processing devices 12. Such embodiments may be of particular value in situations in which a large segment of one or more of the acoustic nerves between the ear(s) and the auditory region 43 has been cut or removed or no longer functions properly, for example as a result of a degenerative disease or a surgical procedure for treatment of a disease. By utilizing two processing devices, restored hearing can be provided to a subject.

Figure 8:
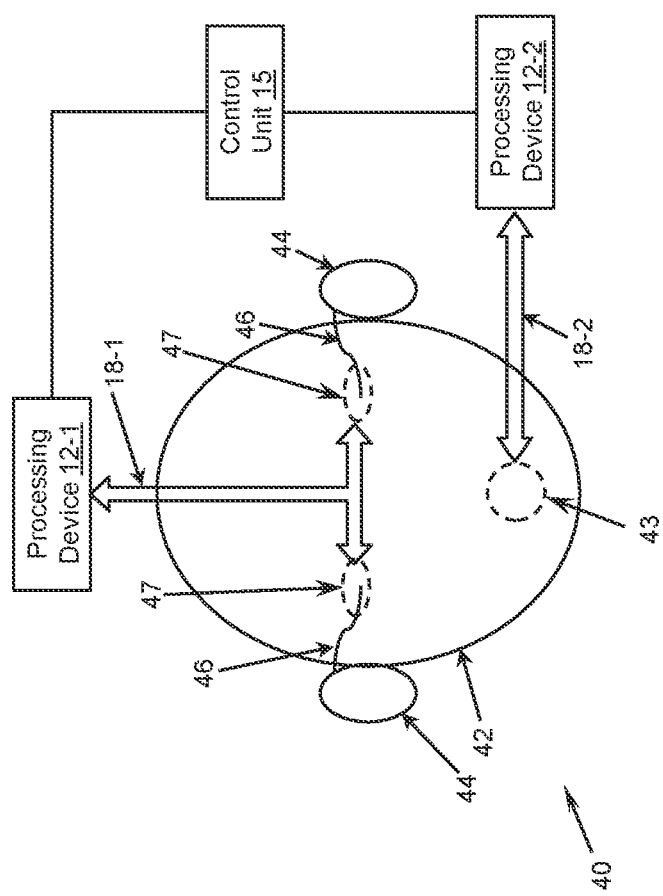
FIG. 8 is a schematic representation of a system similar to the system illustrated in FIG. 1 but in which a pair of processing devices interfacing with different respective regions of the brain of the subject are deployed, according to an embodiment of the present invention.

FIG. 8 schematically illustrates a non-limiting embodiment that utilizes first and second processing devices, designated as processing devices 12-1, 12-2. In the illustrated embodiment, the pathway between the ears 44 and the auditory region 43 has been severed, represented here by the absence of the majority of the acoustic nerves that connect between the ears and the auditory region 43. This may be due, for example, to a physiological defect in which the acoustic nerves 46 do not function properly, or to the physical absence of the nerve segment (for example due to a physiological defect in which nerve segments are missing, or due to treatment of a disease). The processing devices 12-1, 12-2 in combination can, in certain embodiments, operate similar to the processing device 12 to act as a bridge between the ears and the auditory region 43 (or acoustic nerve bypass) whereby nerve impulses generated in response to auditory stimulation of the ears 44 can reach the auditory region 43 via the processing devices 12-1, 12-2.

The first processing device 12-1 is communicatively coupled to the acoustic nerves 46, via an interface 18-1 (which can be similar in structure and operation to any of the interfaces 18 described above), at a portion 47 of the acoustic nerves 46 that is in proximity to the ear 44 (e.g., at or near the cochlea). The first processing device 12-1 is operative to receive nerve impulses, generated in response to auditory stimulation of the ear 44, that are to be transmitted to the auditory region 43 via the acoustic nerves 46, and convert those nerve impulses to audio signal(s) (similar to as described above). In certain embodiments, the processing device 12-1 can obtain signals representative of the nerve impulses via the interface 18-1, which may include one or more EOSFETs at the subject interfacing portion of the interface 18-1 for measuring or sampling the nerve impulses and producing electrical signals in response thereto. The processing device 12-1 can then convert those signals to audio signal(s) using the techniques discussed above.

The second processing device 12-2 can be communicatively coupled to the auditory region 43, for example via implantation of a subject interfacing portion of an interface 18-2 at or on the auditory region 43, or via implantation of the second processing device 12 at or on the auditory region 43. The interface 18-2 can be similar in structure and operation to any of the interfaces 18 described above. The two processing devices 12-1, 12-2 are linked or connected to each other, for example indirectly via the control unit 15 as illustrated, or directly via any suitable data connection means (for example a data bus or the like). The second processing device 12-2 is operative to receive the audio signal(s) generated by the first processing device 12-1, and to convert the received audio signal(s) to nerve impulses, and to provide those nerve impulses to the auditory region 43 (via the interface 18-2 according to any suitable technique including the techniques described above) such that the subject 40 perceives the sound captured by the ears 44 (i.e., the vibrations funneled by the outer ear to the eardrum). In certain embodiments, the processing device 12-2 converts the generated audio signal(s) to corresponding electrical signals, and the processing device 12-2 provides those electrical signals to the subject interfacing portion of the interface 18-2, which may include one or more EOSCs, to stimulate the auditory region 43 in accordance with the electrical signals.

Each of the processing devices 12-1 and 12-2 is similar in structure to the processing device 12 described above, i.e., each of the processing devices 12-1 and 12-2 includes one or more processors coupled to a computerized storage medium. In certain embodiments, either or both of the processing devices 12-1, 12-2 is further operative to modify audio signals in a manner similar to the signal modification performed by the processing device 12 described above. For example, the first processing device 12-1 may modify the generated audio signal(s) (converted from nerve impulses by the first processing device 12-1) and then send the modified audio signal(s) to the second processing device 12-2. Alternatively or in addition to the first processing device 12-1 modifying the generated audio signal(s), the second processing device 12-2 may modify the generated audio signal(s) received from the first processing device 12-2, and then convert the modified audio signal(s) to nerve impulses.

In certain embodiments, either or both of the processing devices 12-1, 12-2 can be linked to an external storage/memory (similar to external storage/memory 32 in FIG. 7). In other embodiments, either or both of the processing devices 12-1, 12-2 can include or be linked to a Tx/Rx unit, similar to the Tx/Rx unit 30 in FIG. 7, that provides a communication/network interface for transmitting/receiving data to/from (i.e., exchanging data with) a communication network. In such embodiments, either or both of the processing devices 12-1, 12-2 can communicate (i.e., exchange data) with a remote server system (such as server system 34) via the communication network.

Note that the embodiments described with reference to FIG. 8 are also applicable to situations in which the auditory pathway between the ears and the brain are still intact, i.e., the nerve 46 between each of the ears 44 and the auditory region 43 is still intact. In such situations, either or both of the nerves 46 can be interfaced with (e.g., tapped) by the processing devices 12-1 and 12-2 in two locations/regions. For example, the first device 12-1 can interface with a first portion of one of the nerves 46 that is in proximity to one of the ears 44 (e.g., at or near the cochlea), and the second device 12-2 can interface with a second portion of that nerve 46 that connects to the auditory region 43. The intervening segment or segments of the nerve (that connects between the first and second portions of the nerve) can then optionally be disabled or damped to restrict transmission between the two portions.

It is also noted that in certain embodiments, only one side of one or both of the nerves 46 leading from the auditory region 43 is interfaced with a processing device 12 (or 12-1 or 12-2 depending on the deployment configuration). For example, in the configuration of FIG. 8, embodiments are contemplated in which only one processing device (the processing device 12-2) is deployed and interfaces with a portion of the auditory nerve 46 that connects to the auditory portion 43. In such embodiments, the processing device is configured to feed nerve impulses to the brain so as to be interpreted as sound.

It is noted that although the processing device 12 (or 12-1 or 12-2 depending on the deployment configuration) has thus far been described as the computing device that generally performs signal modification, for example according to a set of signal modification (manipulation) rules, such signal modification may in fact be performed by any computing device that is connected with the processing device 12 (or 12-1 or 12-2). For example, the server system 34 can be configured to receive signals from the processing device 12 and to modify those signals according to a set of signal modification (manipulation) rules and then send the modified signals back to the processing device 12 for further processing or nerve transmission.

Although some of the embodiments of the present invention described thus far have pertained to utilizing a processing device to convert one or more audio signals (representative of one or more sounds) to a sequence of nerve impulses, and then utilizing the processing device to provide the sequence of nerve impulses to the auditory region of the brain such that the subject audially perceives the one or more sounds, situations may arise in which the subject may wish to perceive silence. As mentioned above, in certain scenarios the one or more sounds are inaudible sounds, such that the subject perceives nerve impulses that are generated from audio signals representative of the inaudible sounds as silence. However, in cases where the sounds are audible sounds, the subject may still wish to perceive silence. Therefore, it is preferable that the subject 40 can controllably actuate the processing device 12 to selectively provide the sequence of nerve impulses to the auditory region of the brain, and further preferable that the subject 40 can controllably actuate the processing device 12 to refrain from providing the sequence of nerve impulses to the auditory region of the brain such that the subject does not audially perceive the one or more sounds and instead perceives silence. Thus, in certain embodiments, the subject can control whether or not the processing device 12 provides generated nerve impulses to the auditory region 43. This control functionality can be provided, for example, via the control unit 15.

Although the embodiments of the present invention are of particular use when applied within the context of human hearing, embodiments of the present disclosure may be equally applicable to hearing in non-human animal subjects, including, but not limited to, other primate species (e.g., monkeys, gorillas, etc.), canine species, feline species, reptile species, bird species, marine/aquatic species, etc. In such non-human applications, nerve impulses can be collected via the same or similar interfacing methods discussed above, and converted to digital sounds by the processing device 12 using a species-specific impulse-sound mapping. Any resultant audio signals can, for example, be output to another system for further processing or use. For example, the audio signals generated from nerve impulses in a canine subject can be provided for playback to be heard by a human subject, or can be converted to nerve impulses using a human impulse-sound mapping function and provided to the acoustic nerves of a human subject such that the human subject can hear sounds as perceived by the canine subject.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, non-transitory storage media such as a magnetic hard-disk and/or removable media, for storing instructions and/or data. Optionally, a network connection is provided as well. A display and/or a user input device such as a keyboard or mouse are optionally provided as well.

For example, any combination of one or more non-transitory computer readable (storage) medium(s) may be utilized in accordance with the above-listed embodiments of the present invention. A non-transitory computer readable (storage) medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

As will be understood with reference to the paragraphs and the referenced drawings, provided above, various embodiments of computer-implemented methods are provided herein, some of which can be performed by various embodiments of apparatuses and systems described herein and some of which can be performed according to instructions stored in non-transitory computer-readable storage media described herein. Still, some embodiments of computer-implemented methods provided herein can be performed by other apparatuses or systems and can be performed according to instructions stored in computer-readable storage media other than that described herein, as will become apparent to those having skill in the art with reference to the embodiments described herein. Any reference to systems and computer-readable storage media with respect to the following computer-implemented methods is provided for explanatory purposes, and is not intended to limit any of such systems and any of such non-transitory computer-readable storage media with regard to embodiments of computer-implemented methods described above. Likewise, any reference to the following computer-implemented methods with respect to systems and computer-readable storage media is provided for explanatory purposes, and is not intended to limit any of such computer-implemented methods disclosed herein.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

As used herein, the singular form "a", "an" and "the" include plural references unless the context clearly dictates otherwise. For example, reference to a single nerve can also refer to a nerve pair. Furthermore, reference to both nerves of a nerve pair can also refer to a single nerve, unless the context clearly dictates otherwise.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The above-described processes including portions thereof can be performed by software, hardware and combinations thereof. These processes and portions thereof can be performed by computers, computer-type devices, workstations, processors, micro-processors, other electronic searching tools and memory and other non-transitory storage-type devices associated therewith. The processes and portions thereof can also be embodied in programmable non-transitory storage media, for example, compact discs (CDs) or other discs including magnetic, optical, etc., readable by a machine or the like, or other computer usable storage media, including magnetic, optical, or semiconductor storage, or other source of electronic signals.

The processes (methods) and systems, including components thereof, herein have been described with exemplary reference to specific hardware and software. The processes (methods) have been described as exemplary, whereby specific steps and their order can be omitted and/or changed by persons of ordinary skill in the art to reduce these embodiments to practice without undue experimentation. The processes (methods) and systems have been described in a manner sufficient to enable persons of ordinary skill in the art to readily adapt other hardware and software as may be needed to reduce any of the embodiments to practice without undue experimentation and using conventional techniques.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for use with an animal subject having a brain that includes an auditory region that is responsible for auditory perception, the method comprising:
    interfacing a processing device with the auditory region of the brain;
    receiving, by the processing device, nerve impulses transmitted to the auditory region of the brain in response to sound collected by at least one ear of the subject; and
    processing, by the processing device, the received nerve impulses by converting the received nerve impulses to at least one audio signal so as to generate the at least one audio signal from the received nerve impulses, wherein the generated at least one audio signal is representative of what the subject hears in response to the sound being collected by the at least one ear of the subject, wherein the processing the received nerve impulses includes applying to the received nerve impulses at least one mapping that maps between nerve impulses and audio signals, and wherein the at least one mapping is a one-to-one mapping such that each nerve impulse is mapped to a corresponding audio signal.

2. The method of claim 1, wherein the interfacing includes: implanting at least a portion of a machine-subject interface in the subject in association with the auditory region of the brain so as to provide communication between the processing device and the auditory region of the brain.

3. The method of claim 1, further comprising: sending data representative of the generated at least one audio signal to at least one of: i) a computerized storage device communicatively coupled with the processing device, or ii) a computerized server system communicatively coupled with the processing device via one or more communication networks.

4. The method of claim 1, further comprising: modifying the generated at least one audio signal to produce a modified at least one audio signal.

5. The method of claim 4, further comprising:
    converting the modified at least one audio signal into one or more nerve impulses; and
    providing the one or more nerve impulse to the auditory region of the brain so as to modify what the subject hears in response to the sound being collected by the at least one ear of the subject.

6. The method of claim 5, wherein providing the one or more nerve impulses to the auditory region of the brain includes transmitting the one or more nerve impulses along one or more nerves connected with the auditory region of the brain.

7. The method of claim 1, further comprising: implanting the processing device in the subject.

8. The method of claim 1, wherein the processing device is external to the subject.

9. A system for use with an animal subject having a brain that includes an auditory region that is responsible for auditory perception, the system comprising:
- a processing device; and
- a machine-subject interface for interfacing the processing device with the auditory region of the brain,
- wherein the processing device is configured to:
  - receive nerve impulses transmitted to the auditory region of the brain in response to sound collected by at least one ear of the subject, and
  - process the received nerve impulses by converting the received nerve impulses to at least one audio signal so as to generate the at least one audio signal from the received nerve impulses, wherein the at least one audio signal is representative of what the subject hears in response to the sound being collected by the at least one ear of the subject, wherein the processing device is configured to process the received nerve impulses by applying to the received nerve impulses at least one mapping that maps between nerve impulses and audio signals, and wherein the at least one mapping is a one-to-one mapping such that each nerve impulse is mapped to a corresponding audio signal.

10. The system of claim 9, wherein at least a portion of the machine-subject interface is configured to be implanted in the subject in association with the auditory region of the brain so as to provide communication between the processing device and the auditory region of the brain.

11. The system of claim 9, wherein the processing device is further configured to: send data representative of the generated at least one audio signal to at least one of:
  - i) at least one computerized storage device communicatively coupled with the processing device, or
  - ii) at least one remote server system communicatively coupled with the processing device via one or more communication networks.

12. The system of claim 11, wherein the processing device is further configured to: modify the generated at least one audio signal to produce a modified at least one audio signal.

13. The system of claim 12, wherein the processing device is further configured to: convert the modified at least one audio signal into one or more nerve impulses, and provide the one or more nerve impulse to the auditory region of the brain so as to modify what the subject hears in response to the sound being collected by the at least one ear of the subject.

14. The system of claim 13, wherein the processing device is configured to provide the one or more nerve impulses to the auditory region of the brain by transmitting the one or more nerve impulses along one or more nerves connected with the auditory region of the brain.

15. A method for use with an animal subject having a brain that includes an auditory region that is responsible for auditory perception, the method comprising:
- interfacing a processing device with the auditory region of the brain;
- processing, by the processing device, at least one audio signal representative of at least one sound to convert the at least one audio signal to a sequence of nerve impulses, wherein the processing the at least one audio signal includes applying to the at least one audio signal at least one mapping having data that maps between nerve impulses and audio signals, wherein the at least one mapping is a one-to-one mapping such that each audio signal is mapped to a corresponding nerve impulse; and
- selectively providing the sequence of nerve impulses to the auditory region of the brain such that the subject audially perceives the at least one sound.

16. The method of claim 15, wherein the at least one sound is inaudible to the subject.

17. The method of claim 15, wherein the at least one mapping is generated by comparing a format of nerve impulses to one or more audio signals.

18. A system for use with an animal subject having a brain that includes an auditory region that is responsible for auditory perception, the system comprising:
- a processing device; and
- a machine-subject interface for interfacing the processing device with the auditory region of the brain,
- wherein the processing device is configured to:
  - process at least one audio signal representative of at least one sound, by applying to the at least one audio signal at least one mapping having data that maps between nerve impulses and audio signals, to convert the at least one audio signal to a sequence of nerve impulses, wherein the at least one mapping is a one-to-one mapping such that each audio signal is mapped to a corresponding nerve impulse, and
  - selectively provide the sequence of nerve impulses to the auditory region of the brain via the machine-subject interface such that the subject audially perceives the at least one sound.

19. The system of claim 18, wherein the at least one sound is inaudible to the subject.

20. The system of claim 18, wherein the at least one mapping is generated by comparing a format of nerve impulses to one or more audio signals.

* * * * *